United States Patent
Chen et al.

(10) Patent No.: US 10,538,507 B2
(45) Date of Patent: Jan. 21, 2020

(54) PREPARATION PROCESS FOR HIGH-PURITY DABIGATRAN ETEXILATE

(71) Applicants: ZHEJIANG HUAHAI PHARMACEUTICAL CO., LTD, Taizhou (CN); ZHEJIANG HUAHAI ZHICHENG PHARMACEUTICAL CO., LTD., Linhai (CN)

(72) Inventors: Lingjie Chen, Linhai (CN); Wenling Zhang, Taizhou (CN); Peng Wang, Taizhou (CN)

(73) Assignees: ZHEJIANG HUAHAI PHARMACEUTICAL CO., LTD, Taizhou (CN); ZHEJIANG HUAHAI ZHICHENG PHARMACEUTICAL CO., LTD., Linhai (CN)

( * ) Notice: Subject to any disclaimer, the term of this patent is extended or adjusted under 35 U.S.C. 154(b) by 0 days.

(21) Appl. No.: 16/301,769

(22) PCT Filed: May 24, 2017

(86) PCT No.: PCT/CN2017/085750
§ 371 (c)(1),
(2) Date: Nov. 15, 2018

(87) PCT Pub. No.: WO2017/202341
PCT Pub. Date: Nov. 30, 2017

(65) Prior Publication Data
US 2019/0152945 A1    May 23, 2019

(30) Foreign Application Priority Data

May 24, 2016 (CN) .......................... 2016 1 0347598

(51) Int. Cl.
C07D 235/04 (2006.01)
C07D 401/12 (2006.01)
B01D 9/00 (2006.01)

(52) U.S. Cl.
CPC ......... *C07D 401/12* (2013.01); *B01D 9/0004* (2013.01); *B01D 9/005* (2013.01); *C07D 235/04* (2013.01)

(58) Field of Classification Search
CPC ..... C07D 401/12; B01D 9/0004; B01D 9/005
USPC ........................................ 549/273; 548/304.4
See application file for complete search history.

(56) References Cited

FOREIGN PATENT DOCUMENTS

| CN | 101189224 | 5/2008 |
|---|---|---|
| CN | 102964307 | 3/2013 |
| CN | 104356111 | 2/2015 |
| EP | 2610251 | 7/2013 |
| WO | WO 2012/077136 | 6/2012 |
| WO | WO 2014/020555 | 2/2014 |
| WO | WO 2014/041559 | 3/2014 |
| WO | WO 2014/192030 | 12/2014 |

OTHER PUBLICATIONS

Extended European Search Report issued in Corresponding European Patent Application No. 17802187, dated Feb. 27, 2019.
International Search Report and Written Opinion issued in International Patent Application No. PCT/CN2017/085750, dated Aug. 15, 2017.

*Primary Examiner* — Taylor V Oh
(74) *Attorney, Agent, or Firm* — Norton Rose Fulbright US LLP

(57) ABSTRACT

Provided is a purifying method for dabigatran etexilate free base, comprising subjecting a dabigatran etexilate free base crude product to water slurrying to obtain a crude product B; then conducting recrystallization on the crude product B with acetone and water to obtain a crude product C; and subsequently, purifying the crude product C with a mixed solvent of tetrahydrofuran and ethyl acetate, filtering and drying to obtain a dabigatran etexilate free base finished product. The purifying method of the present invention can effectively remove various impurities and is suitable for workshop production. Salts and water-soluble organic impurities are removed by purified water slurrying, impurities with a high polarity are removed by purifying with an acetone-water solution, and impurities with a low polarity are removed by purifying with a mixed solvent of tetrahydrofuran and ethyl acetate.

8 Claims, No Drawings

PREPARATION PROCESS FOR HIGH-PURITY DABIGATRAN ETEXILATE

CROSS-REFERENCE TO RELATED APPLICATIONS

This application is a national phase under 35 U.S.C. § 371 of International Application No. PCT/CN2017/085750, filed May 24, 2017, which claims priority to Chinese Patent Application No. 201610347598.0, with the title of "Preparation process for high-purity Dabigatran Etexilate", filed with the China National Intellectual Property Administration on May 24, 2016. The contents of each referenced patent application are incorporated herein by reference in their entirety.

FIELD OF THE INVENTION

The present invention relates to the field of drug synthesis technology, in particular to a process for purification of high-purity dabigatran etexilate.

BACKGROUND OF THE INVENTION

Dabigatran etexilate, a prodrug of dabigatran, is a novel synthetic direct thrombin inhibitor developed by Germany Boehringer Ingelheim, and belongs to non-peptide thrombin inhibitor. Its dosage form, dabigatran etexilate capsule, was approved for marketing in Europe in March 2008 and became the first new type of oral anticoagulants approved for marketing in the past 50 years after warfarin. Its structural formula is:

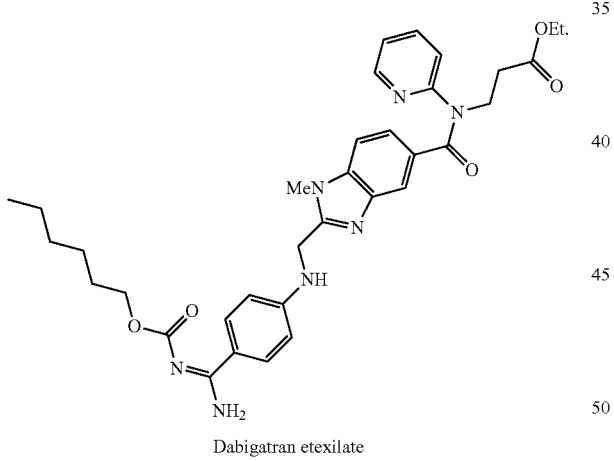

Dabigatran etexilate

There are many reports on the preparation of dabigatran etexilate. At present, the most focused and used method in the industry is to use 3-({2-[(4-Carbamimidoyl-phenylamino)-methyl]-1-methyl-1H-benzoimidazole-5-carbonyl}-pyridin-2-yl-amino)-propionic acid ethyl ester hydrochloride (abbreviation: Amine salts) and n-hexyl chloroformate as starting materials, and acylate to dabigatran etexilate with the alkaline reagent in organic solvents.

During the preparation or storage, some hydrolysis impurity (see patent CN104356111), methyl ester impurity (ethyl ester converted to methyl ester), alcoholysis impurity (see patent CN102964307) and the like are easily generated in dabigatran etexilate. The structures of specific impurity are as follows:

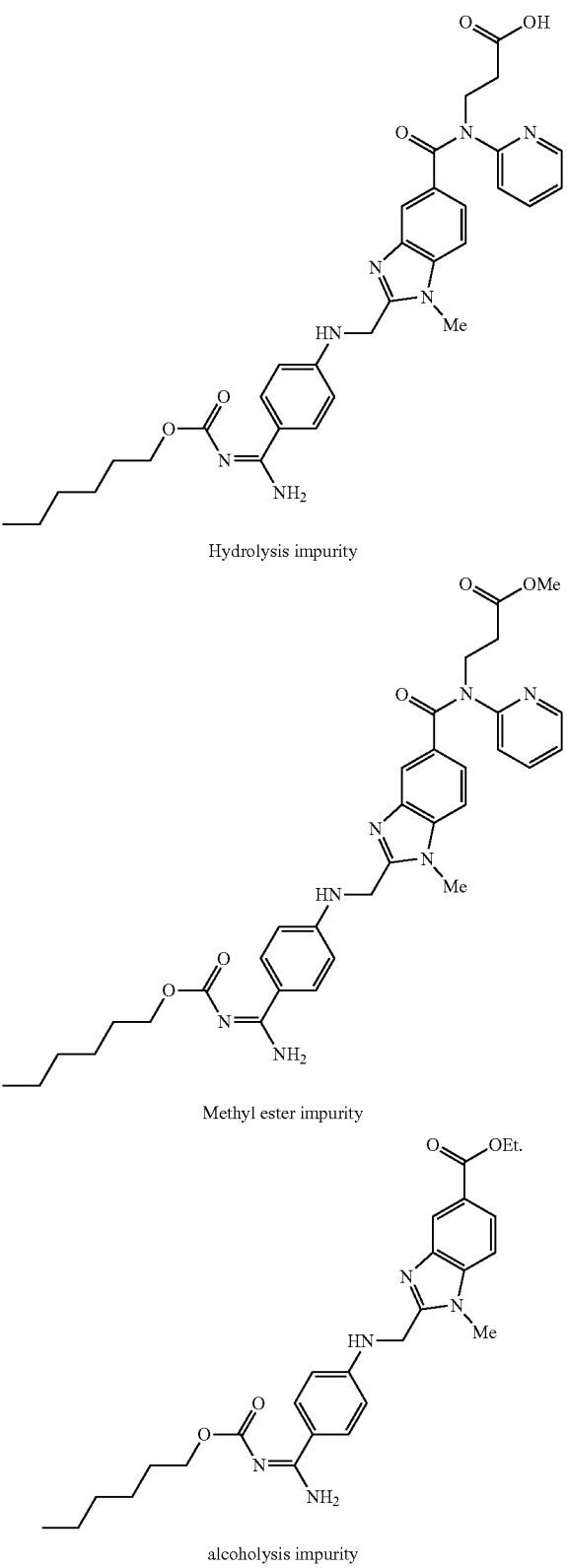

These impurities have quite different chemical properties, so it is very difficult to remove them in one single method. The acetone/water reaction system is selected for the preparation of dabigatran etexilate. The solubility of the alcoholysis impurity in acetone/water system is poor. High purity dabigartran etexilate could not be obtained without effective purification steps.

The patent CN101189224B described a purification method of dabigatran etexilate, comprising: dissolving dabigatran etexilate in ethyl acetate at reflux temperature, cooling the system to 30-35° C. followed by 15-20° C. with stirring, and filtering to get a precipitate; or dissolving dabigatran etexilate in a mixture of acetone/water (80:20), cooling the system to 30° C. and filtering; cooling a filtrate to −9° C., then adding a mixture of acetone/water (80:20) of −9° C. into the filtrate with stirring; filtering to get a precipitate, washing the precipitate with the mixture of acetone/water (80:20) of −9° C. and drying to obtain dabigatran etexilate. This purification method must be repeated for many times, so that the methyl ester impurity can be reduced to a lower level, but the alcoholysis impurity is not substantially removed.

The purification method of dabigatran etexilate was also disclosed in WO2012077136. The disclosed process involves acetone was added to crude product of dabigatran etexilate and stirred to get a clear solution; water was added to the obtained solution to precipitate, filtered, washed the precipitate with water and methyl tert-butyl ether respectively, and then obtained crude product 2 of dabigatran etexilate; a mixture of crude product 2 of dabigatran etexilate and ethyl acetate was heated to reflux temperature with stirring, filtered the reaction mixture through the hyflow bed, washed the bed twice with hot ethyl acetate; ethanol was added to in the filtrate. The reaction mixture was further heated to reflux temperature and stirred, cooled the reaction mixture to 25-35° C., stirred, filtered the solid, washed with ethyl acetate and dried to get pure dabigatran etexilate with a purity of 99.58%. This method uses methyl tert-butyl ether and hot ethyl acetate washing, which has high safety risk in workshop production, and the purity of the product cannot reach the level of the invention.

Another purification method of dabigatran etexilate was disclosed in example 11 of WO2014041559. In this method, crude product of dabigatran etexilate was purified by stirring with a mixture of acetone/with water (8:8 vol), followed by recrystallization from ethyl acetate and ethanol (7:0.3 vol) to obtain the pure dabigatran etexilate with a purity of 99.7%. In another method that described in example 12, the crude product was purified by recrystallization with a mixture of ethyl acetate and acetone (7.0:3.0 vol) to get dabigatran etexilate, purity 99.7%. The method has less effect on removing alcoholysis impurity than the present invention, and the purity of the product cannot reach the level of the invention.

To sum up, the methods for purifying dabigatran etexilate reported in the literature have the problems of complicated operation, low safety factor and difficulty in substantially removing all kinds of impurities completely. Therefore, it is very necessary to develop a purification method that is easy to operate and can greatly reduce all kinds of impurities existing in dabigatran etexilate. In addition, the preparation of high-purity dabigatran etexilate also provides a basis for the preparation of high-purity dabigatran etexilate mesylate.

SUMMARY OF THE INVENTION

The present invention provides a purification method for high-purity dabigatran etexilate. According to this process, dabigatran etexilate with a purity of no less than 99.8% can be obtained.

The invention finds that high-purity dabigatran etexilate can be obtained by the following steps:

a) slurrying the dabigatran etexilate crude product with water to obtain a crude product B;

b) recrystallizing the crude product B with acetone and water to obtain a crude product C;

c) purifying the crude product C with a mixture of tetrahydrofuran and ethyl acetate, filtering and drying to obtain high-purity dabigatran etexilate.

Preferably, in step a), the ratio of mass of crude product of dabigatran etexilate to volume of water is 1:10-20 g/ml.

Preferably, the ratio of mass of crude product of dabigatran etexilate to volume of acetone is 1:4-10 g/ml.

Preferably, in step b), the volume ratio of water to acetone is 1:1-1:3.

Preferably, the ratio of mass of crude product of dabigatran etexilate to volume of tetrahydrofuran is 1:0.5-1.5 g/ml.

Furthermore, in step c), the volume ratio of tetrahydrofuran to ethyl acetate is 1:10-20.

Compared with the prior art, the purifying method described in the present invention can effectively remove various impurities and is suitable for workshop production. Salt and water-soluble organic impurities can be removed by water slurrying, high-polarity impurities can be removed by purifying with acetone aqueous solution, and low-polarity impurities can be removed by purifying with the mixture of tetrahydrofuran and ethyl acetate.

The present invention also provides a pharmaceutical composition, including dabigatran etexilate with content no less than 99.8%. The single impurity content is less than 0.05%, in which the content of alcoholysis impurity (as shown in formula I) is no more than 0.05%, the content of methyl ester impurity (as shown in formula II) is no more than 0.05%. All of the contents are determined by HPLC area normalization method, wherein the structural formula of impurity I and II are as follows:

Formula I

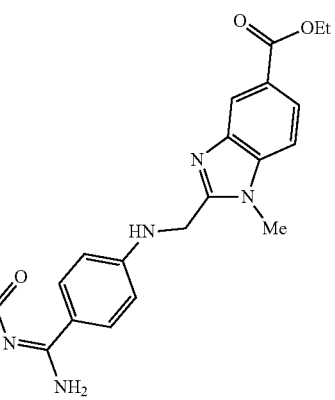

Formula II

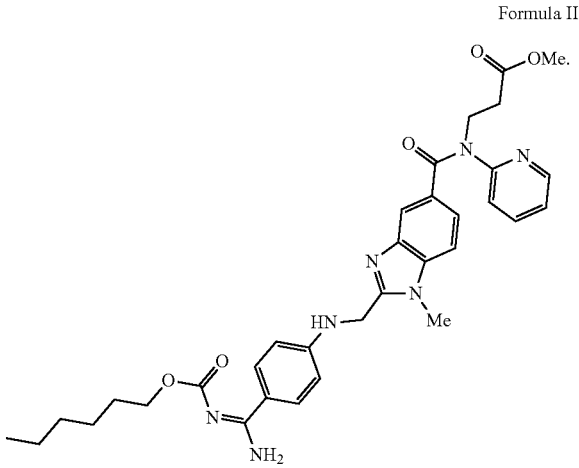

The present invention also provides a process for purification high-purity dabigatran etexilate with content of dabigatran etexilate no less than 99.8%. The content of single impurity is less than 0.05%, in which the content of alcoholysis impurity is no more than 0.05%, and the content of methyl ester impurity is no more than 0.05%. This method includes:
a) slurrying crude product of dabigatran etexilate with water to obtain a crude product B;
b) recrystallizing the crude product B with acetone and water to obtain a crude product C; and
c) purifying the crude product C with a mixture of tetrahydrofuran and ethyl acetate, filtering and drying to obtain high-purity dabigatran etexilate.

Preferably, a process for the purification of high-purity dabigatran etexilate is provided, comprising:
a) adding crude product of dabigatran etexilate into water, slurrying at 5-30° C., and filtering after slurrying for 1-2 h to get a crude product B;
b) adding the crude product B into acetone, heating up to 20-50° C., then adding water dropwise into the solution, cooling the solution to 0-10° C., and filtering to get a crude product C; and
c) adding the crude product C into a mixture of tetrahydrofuran and ethyl acetate, heating up to 50-70° C. to dissolve, and then cooling to 40-45° C., preferably adding a seed crystal, slowly cooling to 0-5° C., then filtering, drying the filter cake at 40-50° C. under vacuum to obtain high-purity dabigatran etexilate.

DETAILED DESCRIPTION OF EMBODIMENTS

The embodiments of the present invention will be illustrated in more detail in combination with the following examples. The embodiments of the present invention comprise but not limited to the following examples, which should not be deemed as the limitation to the protection scope of the present invention.

Example 1

198 g acetone was added into a reaction flask A, then 42 g of Amine salts was added, and the system was stirred at 10-20° C. 210 g of purified water and 32.5 g of potassium carbonate were added into a reaction flask B, and the system was cooled to 10-15° C. A potassium carbonate solution was added slowly into the reaction flask A at 10-20° C. Then 19.4 g of n-hexylchloroformate was added dropwise. The system was filtered after stirring at 10-15° C. for 1.5 h to get 81.4 g of crude product A.

820 g of purified water was added into a reaction flask, then 81.4 g of crude product A was added at 15-25° C., and the system was filtered after stirring for 2 h to get 60.0 g of crude product B.

300 ml acetone was added into a reaction flask, then 60.0 g of the crude product B was added, the system was heated to 45-55° C. after stirring. Then 100 g of purified water was added dropwise into the system at 20-30° C. After the addition was completed, the system was cooled to 0-5° C. and kept for 1 h, followed by filtering to get 55.2 g of crude product C.

560 ml of ethyl acetate and 56 ml of tetrahydrofuran were pumped into a reaction flask. 55.2 g of the crude product C was added into the reaction flask, and the system was heated to 50-60° C. to obtain a clear solution. The solution was slowly cooled to 40-45° C., and 1 g of seed crystal was added. After keeping at 40-45° C. for 1 h, the system was cooled and kept at 5° C. for 1 h. The system was filtered to get a filter cake, and the filter cake was dried under vacuum at 40-50° C. to get 42.21 g of high-purity dabigatran etexilate, yield 80%, purity 99.8%, the content of methyl ester impurity 0.04%, and the content of alcoholysis impurity 0.03%.

Example 2

198 g of acetone was added into a reaction flask A, then 42 g of Amine salts was added, and the system was stirred at 10-20° C. 210 g of purified water and 24.9 g of sodium carbonate were added into a reaction flask B, and the system was cooled to 10-15° C. A sodium carbonate solution was added slowly into the reaction flask A at 10-20° C. After 19.4 g of n-hexyl chloroformate was added dropwise, and the system was filtered after stirring at 10-15° C. for 1.5 h to get 78.3 g of crude product A.

1560 g of purified water was added into a reaction flask, cooled to 15-25° C., then 78.3 g of the crude product A was added, and the system was filtered after stirring for 2 h to get 57.6 g of crude product B.

570 ml acetone was added into a reaction flask, and then 57.6 g of the crude product B was added. The system was heated to 45-55° C. after stirring. 570 g of purified water was added dropwise into the system at 20-30° C. After the addition was completed, the system was cooled to 0-5° C. and kept for 1 h, followed by filtering to get 53.4 g of crude product C.

1600 ml ethyl acetate and 80 ml tetrahydrofuran were pumped into a reaction flask. 53.4 g of the crude product C was added into the reaction flask and the system was heated 50-60° C. to obtain a clear solution. The solution was slowly cooled to 40-45° C., and 1 g seed crystal was added. After keeping at 40-45° C. for 1 h, the system was cooled to 5° C. and kept for 1 h. The system was filtered to get a filter cake, and the filter cake was dried under vacuum at 40-50° C. to get 36.3 g of high-purity dabigatran etexilate, yield 74%, purity 99.9%, the content of methyl ester impurity 0.02%, and the content of alcoholysis impurity 0.01%.

The invention provides a process for purification purifying of high-purity dabigatran etexilate, which has been described in the examples. It is obvious to those skilled in the art that the present invention can be realized by modification or appropriate amendment and combination of the methods described herein without departing from the content, spirit and scope of the invention. It is particularly important to note that all similar replacements and modifications are obvious to those skilled in the art and are considered to be included in the spirit, scope and content of the present invention.

The invention claimed is:

1. A process for the preparation of high-purity dabigatran etexilate comprising:
   a) adding a crude product of dabigatran etexilate into water, slurrying at 5-30° C., and filtering after slurrying for 1-2 h to get a crude product B;
   b) adding the crude product B into acetone, heating up to 20-50° C. to obtain a clear solution, then adding water dropwise into the solution, cooling the solution to 0-10° C., and filtering to get a crude product C; and
   c) adding the crude product C into a mixture of tetrahydrofuran and ethyl acetate, heating up to 50-70° C. to dissolve, and then cooling to 40-45° C., slowly cooling to 0-5° C., then filtering, drying filter cake at 40-50° C. under vacuum to obtain the high-purity dabigatran etexilate.

2. The process according to claim 1, wherein the ratio of mass of the crude product of dabigatran etexilate to volume of water in step a) is 1:10-20 g/ml.

3. The process according to claim 1, wherein the ratio of mass of the crude product of dabigatran etexilate to volume of acetone is 1:4-10 g/ml.

4. The process according to claim 1, wherein the volume ratio of water to acetone in step b) is 1:1-1:3.

5. The process according to claim 1, wherein the ratio of mass of the crude product of dabigatran etexilate to volume of tetrahydrofuran is 1:0.5-1.5 g/ml.

6. The process according to claim 1, wherein the volume ratio of tetrahydrofuran to ethyl acetate in step c) is 1:10-20.

7. The process according to claim 1, wherein the high-purity dabigatran etexilate comprises dabigatran etexilate with content no less than 99.8%, an alcoholysis impurity of formula I with content no more than 0.05%, and a methyl ester impurity of formula II with content no more than 0.05

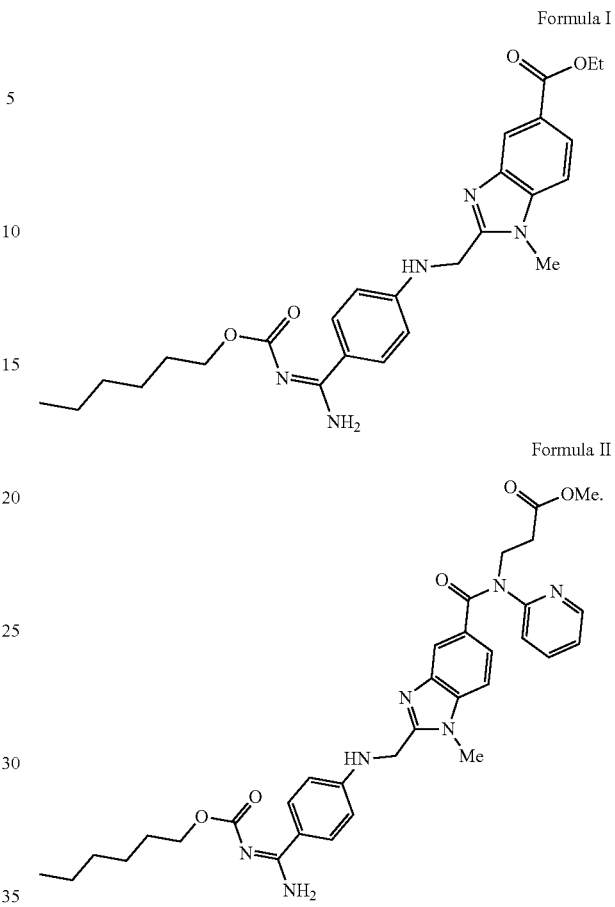

Formula I

Formula II

8. The process according to claim 1, comprising:
   a) adding the crude product of dabigatran etexilate into water, slurrying at 5-30° C., and filtering after slurrying for 1-2 h to get a crude product B;
   b) adding the crude product B into acetone, heating up to 20-50° C. to obtain a clear solution, then adding water dropwise into the solution, cooling the solution to 0-10° C., and filtering to get a crude product C; and
   c) adding the crude product C into a mixture of tetrahydrofuran and ethyl acetate, heating up to 50-70° C. to dissolve, and then cooling to 40-45° C., adding a seed crystal, slowly cooling to 0-5° C., then filtering, drying filter cake at 40-50° C. under vacuum to obtain the high-purity dabigatran etexilate.

* * * * *

UNITED STATES PATENT AND TRADEMARK OFFICE
CERTIFICATE OF CORRECTION

| | | |
|---|---|---|
| PATENT NO. | : 10,538,507 B2 | Page 1 of 2 |
| APPLICATION NO. | : 16/301769 | |
| DATED | : January 21, 2020 | |
| INVENTOR(S) | : Lingjie Chen, Wenling Zhang and Peng Wang | |

It is certified that error appears in the above-identified patent and that said Letters Patent is hereby corrected as shown below:

In the Claims

In Column 7, Claim 7, Line 51, please delete:
"0.05"
And replace with:
"0.05%."

In Column 8, Claim 7, Line 20, please delete:

"
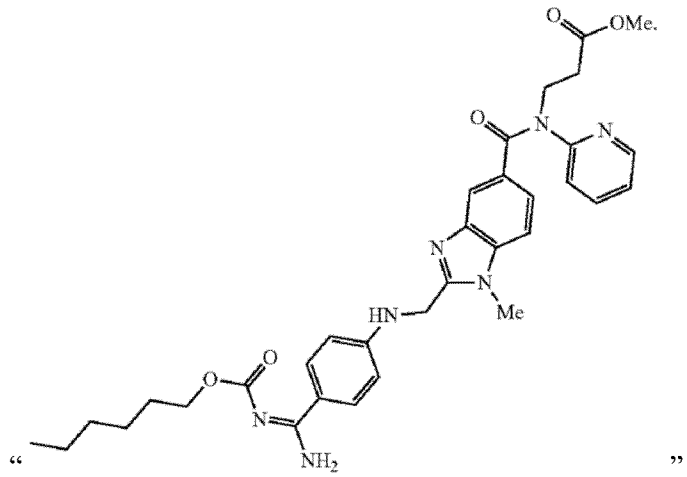
"

And replace with:

Signed and Sealed this
Fifth Day of May, 2020

Andrei Iancu
*Director of the United States Patent and Trademark Office*

CERTIFICATE OF CORRECTION (continued)
U.S. Pat. No. 10,538,507 B2

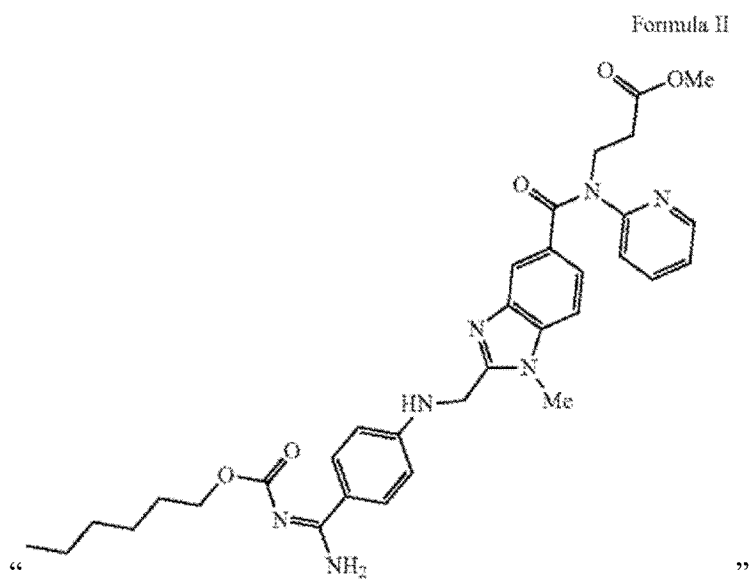

Formula II

""